United States Patent
Craft et al.

(10) Patent No.: US 8,489,366 B2
(45) Date of Patent: Jul. 16, 2013

(54) SYSTEM AND METHOD FOR RADIATION DOSE CONTROL

(75) Inventors: David Craft, Cambridge, MA (US); Thomas Bortfeld, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 1337 days.

(21) Appl. No.: 12/181,712

(22) Filed: Jul. 29, 2008

(65) Prior Publication Data

US 2009/0037150 A1 Feb. 5, 2009

Related U.S. Application Data (60) Provisional application No. 60/962,493, filed on Jul. 30, 2007.

(51) Int. Cl.
*G06F 17/10* (2006.01)

(52) U.S. Cl.
USPC .......................................................... 703/2

(58) Field of Classification Search
USPC ............................................................ 703/2
See application file for complete search history.

(56) References Cited

U.S. PATENT DOCUMENTS

| | | | |
|---|---|---|---|
| 6,757,667 B1 * | 6/2004 | Patel | 706/19 |
| 2005/0207531 A1 * | 9/2005 | Dempsey et al. | 378/65 |
| 2007/0239497 A1 * | 10/2007 | Fertig et al. | 705/7 |

OTHER PUBLICATIONS

Craft et al., Approximating Convex Pareto Surfaces in Multiobjective radiotherapy planning, 2006.*
Hoffmann et al., (Derivative-Free Generation and Interpolation of Convex Pareto Optimal) IMRT plans, 2006).*
Craft et al., "Exploration of tradeoffs in intensity modulated radiotherapy," Phys. Med. Biol. 50. pp. 5857-5868 (2005).
Ruzika et al., "A survey of approximation methods in multiobjective programming," Technical Report, Department of Mathematics, University of Kaiserslautern, (2003).
Klamroth et al., "Unbiased approximation in multicriteria optimization," Math. Methods Oper. Res. 56, pp. 413-437 (2002).
Solanki et al., "Approximating the noninferior set in multiobjective linear programming problems," Eur. J. Oper. Res. 68, pp. 356-373 (1993).

* cited by examiner

*Primary Examiner* — David Silver
*Assistant Examiner* — Andre Pierre Louis
(74) *Attorney, Agent, or Firm* — Quarles & Brady LLP (57) ABSTRACT

A system and method for determining a desired portion of a subject to receive a radiation dose includes iteratively choosing weight vectors to run to gradually build up a Pareto surface (PS). BY examining the current points that have been found on the PS along with the weights used to produce those points, a new vector is produced and run. This process is repeated until a geometric stop tolerance is met.

25 Claims, 3 Drawing Sheets

SYSTEM AND METHOD FOR RADIATION DOSE CONTROL

CROSS-REFERENCE TO RELATED APPLICATIONS

This application is based on, incorporates herein by reference, and claims the benefit of U.S. Provisional Application Ser. No. 60/962,493, filed on Jul. 30, 2007, and entitled, SYSTEM AND METHOD FOR RADIOTHERAPY PLANNING."

STATEMENT REGARDING FEDERALLY SPONSORED RESEARCH

N/A

FIELD OF THE INVENTION

This invention relates generally to systems and methods for developing control plans for radiation dosage and, more particularly, to systems and methods to determine a desired plan for applying a radiation dose.

BACKGROUND OF THE INVENTION

The application of radiation to an individual is commonplace in a number of industries, such as the medical industry, where radiation is used in imaging applications and therapy applications, and the security industry, where radiation is used to perform inspection processes. Regardless of the industry, whenever radiation is applied to a living subject, a balance is sought between the ability to achieve the best results of the process utilizing the radiation, which typically leans toward increased radiation dosage, and the safety of the subject, which typically leans toward decreased radiation dosage.

To this end, a constant difficulty that arises in radiotherapy treatment planning is the patient-specific tradeoff between providing an appropriate radiation dose to a tumor and keeping the healthy tissue dose low. This is traditionally handled by forming a joint objective function that includes an objective that rewards high, uniform dose to the tumor, as well as separate objectives that penalize dose to various healthy organs or tissue. The problem with this approach is that a good set of relative weighting factors on the different objectives is not a priori known, and must be found by the treatment planner using a, time-consuming, iterative, process, often based at least partially on trial and error. Furthermore, a set of weights found for one patient will likely not work well for another patient. Indeed, it has been shown that for a concave tumor phantom and a nearby critical structure, the geometry parameterized by the separation distance and the relative weights that give comparable plans are different for each instance.

Therefore, it would be desirable to have a system and method that allows treatment planners and physicians to understand the tradeoffs for individual patients, while simultaneously avoiding the time-consuming human-iteration loop of searching for a good set of objective function weights.

SUMMARY OF THE INVENTION

The present invention overcomes the aforementioned drawbacks by providing a system and method for calculating well-placed points on a Pareto surface (PS) and applying it to an intensity modulated radiation therapy (IMRT) planning problem. The invention includes an algorithm that uses a feasible set and objective functions that are convex and this condition is satisfied by staying within a linear programming environment. A "sandwiching technique" that finds upper and lower bounds for the PS allows the PS to be iteratively approximated to any specified degree of exactness. The algorithm specifies how to add a single point to the surface to best reduce the surface position uncertainty. These benefits are not available in traditional constraint methods, such as the normal boundary intersection method, the epsilon constraint method, or the uniform weights scalarization approach.

In accordance with the present invention, a method for selecting a desired portion of a subject to receive a radiation dose is disclosed. The method includes selecting a plurality of points on a Pareto surface (PS) using a plurality of weights to identify the plurality of points, iteratively choosing additional weights to run to build up a model of the PS, and examining each point that has been found on the PS along with the weights used to produce the point to determine if the point is indicated a Pareto optimal. The method further includes identifying new weights and repeating the previous steps using the new weights until a Pareto optimal stop tolerance is met.

In accordance with another aspect of the present invention, a method for selecting a desired portion of a subject to receive a radiation dose is disclosed. The method includes selecting a lower bound and an upper bound to sandwich a PS therebetween, performing a convex hulling to obtain a facet representation of the PS, and determining lower distal point (LDP) for each facet. The method also includes calculating a distance from each facet to each LDP, comparing the distance to a threshold value, and repeating the above steps until the distance is below the threshold value for all sides of the PS.

In accordance with yet another aspect of the present invention, a system for selecting a desired portion of a subject to receive a radiation dose is disclosed. The system includes a computer having a computer program that when executed causes the computer to select a plurality of points believed to be on a PS about the desired portion of the subject using a plurality of weights to identify the plurality of points and iteratively choose additional weights to run to build up a model of the PS. The computer is also caused to examine each point that has been selected along with the weights used to produce the point; and identify new weights. Also, the computer is caused to repeat the above steps using the new weights until a geometric stop tolerance is met.

Various other features of the present invention will be made apparent from the following detailed description and the drawings.

BRIEF DESCRIPTION OF THE DRAWINGS

The invention will hereafter be described with reference to the accompanying drawings, wherein like reference numerals denote like elements, and.

DETAILED DESCRIPTION OF THE INVENTION

As will be described, the present invention approaches the multiple objective intensity modulated radiation therapy (IMRT) optimization problem by computing a database of Pareto optimal plans for subsequent exploration. For a given set of objective functions $F_i(x)$, i=1 ... N, a beamlet solution x is Pareto optimal if there does not exist a strictly better feasible solution. A solution y is strictly better than x if $F_i(y) \leq F_i(x)$ for all i, with a strict inequality for at least one i. The algorithm is suitable for moderate dimensional multiobjective problems, for example, N up to 5 or 6.

The computation of a representative set of Pareto optimal solutions is not the only approach to multiobjective programming (MOP). Two other common approaches for handling multiple objectives are goal programming (GP) and lexicographic ordering (LO). These methods require that the decision maker specifies his or her preferences before optimization begins, and based on these preferences, a single Pareto optimal plan is computed, which makes these techniques attractive from a computational standpoint. In GP, objectives are re-expressed as goals. Goals are achieved by minimizing a weighted sum of the deviations from these goals. Based on the set of weights chosen, a single balanced plan is computed. In LO, also called preemptive goal programming, the objectives are prioritized. The first optimization problem minimizes the objective with the highest priority. The result of this serves as a constraint for the next problem, where the objective with the next highest priority is minimized with a constraint that the first objective cannot go above its optimal value in the first solution. This is repeated for subsequent prioritization levels. LO leads to extreme solutions, based on the priority ordering, which may not be desirable by decision makers. Therefore, in accordance with the present invention, the computation of a representative set of Pareto optimal solutions is preferred since it is the only approach that actually shows the tradeoffs to the planners, allowing them to choose a plan with an understanding of the different options available.

The general Pareto MOP can be represented as:

$$\text{MINIMIZE}\{F_i(x)\}, i=1 \ldots N \: x \in X, \qquad \text{Eqn. (1)}$$

where $F_i$ is the ith objective function, x is a vector of decision variables, and X is a convex constraint set in the decision variable space. Whereas single optimization problems have a single solution, MOPs have a set of optimal solutions called the Pareto set. A version of the above MOP formulation specific to IMRT treatment plan optimization can be found in Craft, T. Halabi, and T. Bortfeld, "Exploration of tradeoffs in intensity modulated radiotherapy," Phys. Med. Biol. 50, 5857-5868 (2005), which is incorporated herein by reference.

Equation 1 is shorthand for "find all Pareto optimal solutions with $F_i$ as the objective functions." Typically, the set of all Pareto optimal solutions is not available in closed form. Therefore, a discrete set of points on the PS that approximates the surface well is sought. It should be noted that PS is used herein to refer to the surface in objective function space. That is, PS is the space with one coordinate axis for each objective function $F_i$. Put another way, it could be thought of as the surface of Pareto optimal points in the underlying decision variable x space In settings where the calculation of an individual point on the PS is computationally expensive, there is a motivation to compute a good representation of the surface in as few points as possible. In two dimensions (2D), for example, if the Pareto tradeoff curve is kinked, two end points and a point at the kink produce a sufficient and economical representation of the surface. However, a priori, the shape of the PS is unknown. Nevertheless, as will be explained below, convexity properties of the problem lead to geometric lower and upper bounds on the PS, which can be used to guide to a well-distributed placement of points on the PS.

Scalarization algorithms are a common method for handling equation 1 when the constraint set X is convex and the functions $F_i$ are convex. Under these convexity assumptions, Pareto optimal solutions to equation 1 can be found by solving the following:

$$\text{MINIMIZE} \sum_{i=1}^{N} w_i F_i(x) \qquad \text{Eqn. (2)}$$

$$x \in X.$$

By spanning the entire set of weights $$w_{i \geq 0}, \sqrt{\sum_{i=1}^{N} w^2} = 1,$$

the entire PS can be obtained. However, this is highly impractical, and even a fine discrete sampling is impractical for any number of objectives above 3. Furthermore, there is no guarantee that a pre-specified set of weight vectors to run will lead to a good distribution of points on the PS.

Despite these apparent weaknesses, there are several advantages to using a scalarization method. One is that in IMRT planning, many treatment planning systems (TPS) are designed where such scalarization is done by hand, with planners iteratively changing the weights to find a good plan. Therefore, by developing an algorithm that works on this principle, the algorithm can be hooked up to these solvers, provided they are using convex formulations, with minimal effort. Another advantage is the empirical observation that the solution time for a scalarized problem is much faster than other techniques, which get individual points on the PS of a MOP. In particular, the normal boundary intersection (NBI) method, the normal constraint (NC) method, and the epsilon constraint method, such as described, for example, in S. Ruzika and M. M. Wiecek, "A survey of approximation methods in multiobjective programming," Technical report, Department of Mathematics, University of Kaiserslautern, (2003) incorporated herein by reference, all add hard constraints to the underlying optimization program. It has been observed that these constraints can make the solution process significantly slower. The NBI and NC methods also are designed to populate the PS with an even spread of points regardless of the curvature of the PS, which is not economical. These techniques also clip edge portions off of the PS in dimensions over 2, and thus should be used only when this is acceptable.

On the other hand, the algorithm of the present invention overcomes these problems by sandwiching the PS between a lower and an upper convex approximation. Others, such as K. Klamroth, J. Tind, and M. M. Wiecek, "Unbiased approximation in multicriteria optimization," Math. Methods Oper. Res. 56, 413-437 (2002) and R. S. Solanki, P. A. Appino, and J. L. Cohon, "Approximating the noninferior set in multiobjective linear programming problems," Eur. J. Oper. Res. 68, 356-373 (1993) have used similar approaches. However, the approach of Klamroth et al. is not based on a weighted sum approach, and thus suffers from speed issues for the individual Pareto point solutions. The approach of Solanki et al. does use a weighted sum method for generating individual solutions, but there are a couple of key differences with the algorithm of the present invention. One is that the present invention provides a closed form algebraic solution to the problem of finding the distances between the lower approximation and the upper approximation. On the other hand Solanki et al. relies on a separate linear program for this calculation. The second key difference is in how the boundary of the PS is handled. Solanki et al. uses negative weight vectors, and thus can obtain non-Pareto optimal points. Since each run is expensive, the present invention does not use negative weight vectors, and instead attempts to find the proper weighting vector based on the weight vectors used to create the boundary region being targeting.

In certain applications, the user will opt to not flush out the boundary points of the Pareto set, in which case the issue of dealing with the boundary is irrelevant. In general though, the user typically has formed a set of constraints such that any solution that satisfies those constraints is a potentially viable solution, and hence, the present invention seeks to determine the entire PS given that constraint set.

The algorithm of the present invention relies heavily on the following result from multiobjective programming: if the individual functions $F_i$ are convex and the feasible decision variable space X is convex, then the PS is convex. This means that any hyperplane plane tangent to the PS is a supporting hyperplane, hence, the PS is entirely on one side of the hyperplane. The method of the present invention is applicable to general convex optimization MOPs.

As follows below, in the objective function space, upper-case letters are used for location vectors, such as $\vec{P}$ $\vec{F}$, and lowercase letters are used for direction vectors, such as $\vec{n}$, $\vec{w}$.

As will be explained with respect to FIG. 1, at the highest level, the algorithm referred to herein as PGEN iteratively chooses weight vectors $\vec{w}$ to run to gradually build up the PS. By examining the current points that have been found on the PS along with the weights Used in equation 2 that produced those points, PGEN produces a new weight vector to run, and repeats this process until a geometric stop tolerance is met.

Figure 2:
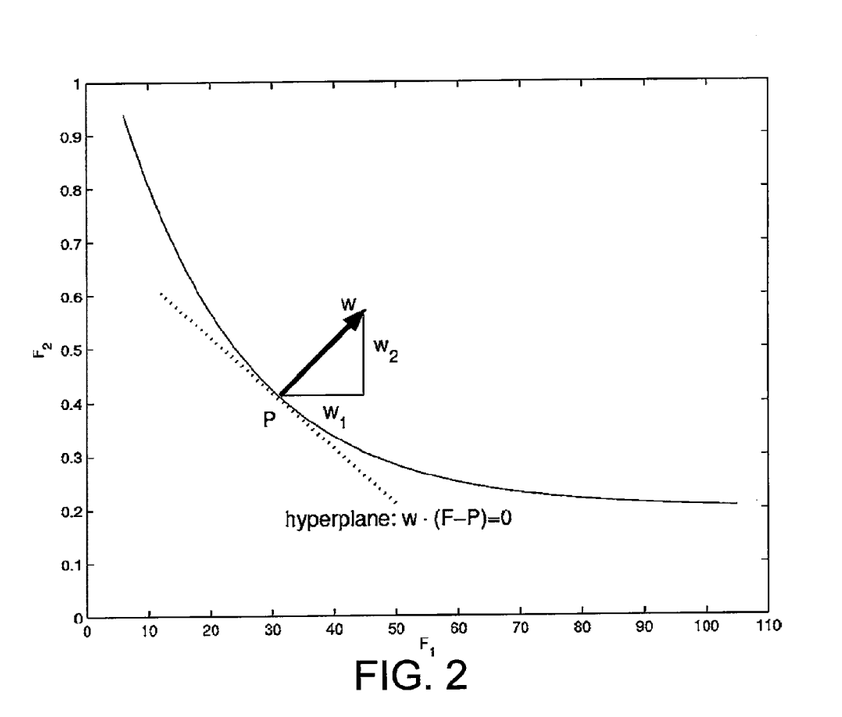
FIG. 2 is a graph showing the hyperplane through the point $\vec{P}$ with normal $\vec{w}$.

Points on the PS and the associated weight vector are written as the pair ($\vec{P}$ $\vec{w}$). Since the PS is convex, for each ($\vec{P}$ $\vec{w}$), the hyperplane through point P with normal $\vec{w}$ is a supporting hyperplane of the PS. That is, it is a lower bound of the PS. This gives, with each new point calculated, a new lower bound on the PS. This is illustrated in FIG. 2, which shows the hyperplane through the point P with normal $\vec{w}$, which is given by the following equation:

$$\vec{w} \cdot (\vec{F} - \vec{P}) = 0 \qquad \text{Eqn. 3;}$$

where $\vec{F} = (F_1, F_2)$ is a lower bound to the PS.

An upper bound is obtained by the convex combination of all of the points thus far found on the PS. The lower and upper bounds are then combined and, at places where the bounds have the largest gap, new points are added to the surface.

Figure 3:
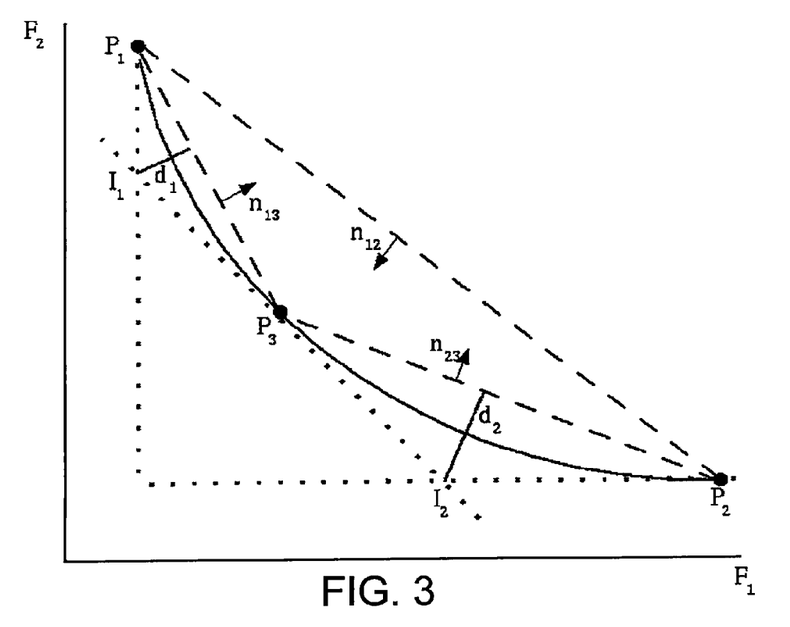
FIG. 3 is an illustration of the PGEN algorithm on a bicriteria optimization problem.

Referring now to FIGS. 2 and 3, various aspects of the algorithm can be described as visualized in 2D. The concepts extend to N dimensions, but nontrivially, particularly when dealing with the boundary of the PS. For simplicity it is assumed that each function is to be minimized with positive weights. Maximization problems are turned into minimization problems with negative weights, but this detail is unnecessary and only complicates the exposition.

Figure 1:
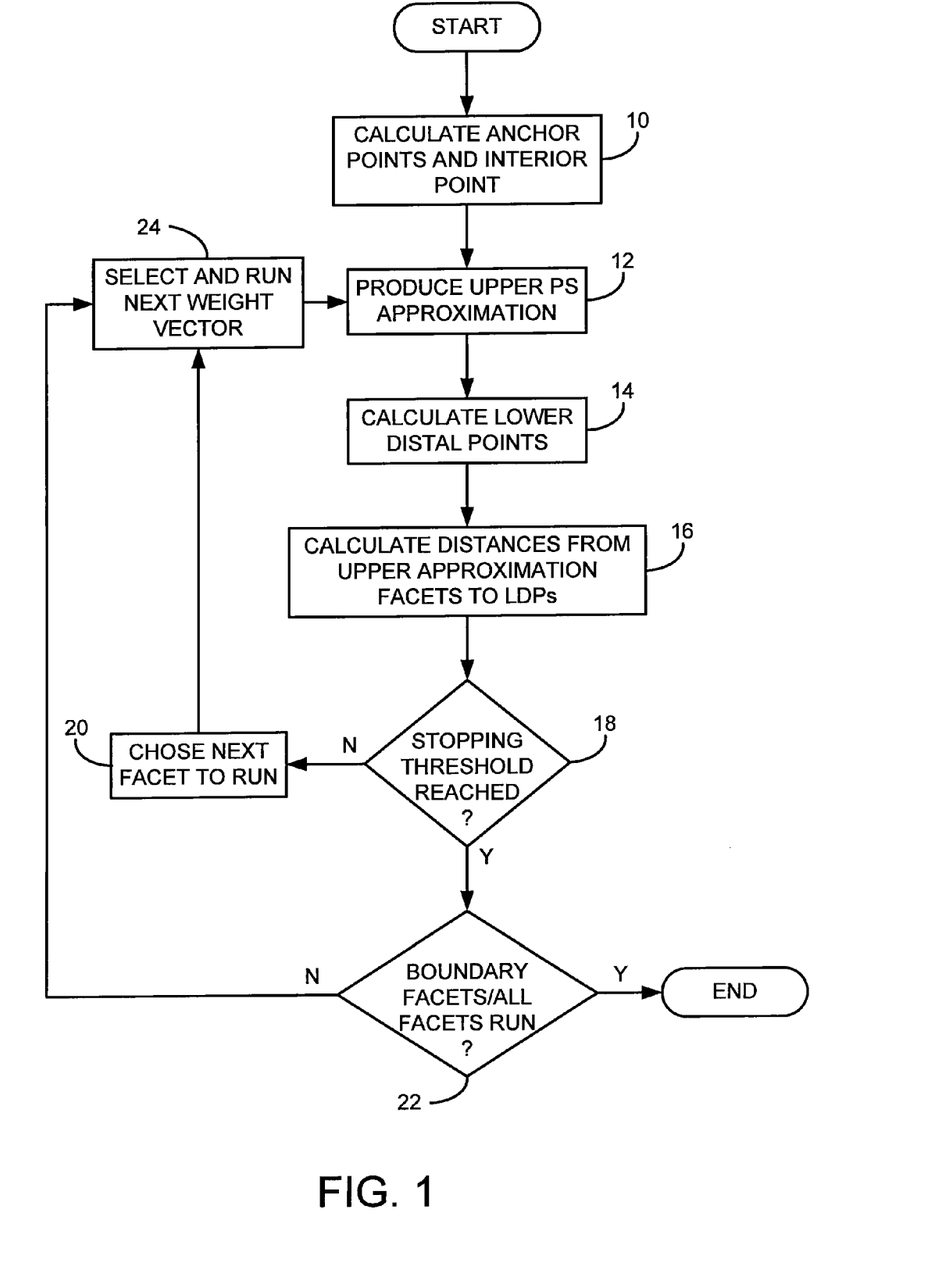
FIG. 1 is a flow chart setting forth the steps for a process in accordance with the present invention.

Referring to FIG. 1, the process is begun by finding anchor points at process block 10. Minimizing each objective function individually, by setting $\vec{w}_i = 1$ for the objective function to minimize and $\vec{w}_i = 0$ for all other objective functions, produces the N anchor points. In FIG. 3, these are the points labeled $P_1$ and $P_2$. These points bound the lower extent of the PS in each respective dimension. After the N anchor points are computed, a single balanced point is computed by either using equal weights on each objective function, or by using the outward-facing normal of the hyperplane through the N anchor points, provided all of the components are non-negative.

Referring to FIG. 3, at this point, points $P_1$ and $P_2$ have been calculated along with an interior point, $\vec{P}_3$. The intersection of the lower bound tangent planes leads to the points $I_1$ and $I_2$ which are called lower distal points (LDPs). In this case, the "I" designation for the points is to stand for intersection. The distances $d_1$ and $d_2$ from these points to the corresponding upper approximation segments are used to select the next $\vec{w}$ vector to run.

As show in FIG. 1, the process continues by performing a convex hulling to produce the upper PS approximation at process block 12. The convex hull of a set of points in N-dimensional (ND) space is the set of all points that can be expressed as convex combinations of the points in the original set. This infinite set is compactly represented as a set of bounding facets, such as line segments in 2D, triangles in 3D, and the like, and their normals. Since it is known that for convex optimization MOPs the PS points lie on the boundary of a convex set, a convex hulling algorithm can be used to obtain a facet representation of the PS. For example, a freely available ND convex hull algorithm called convhulln and available in software such as Qhull can be used. Convhulln takes as input the points and returns the connectivity of those points. That is, the software returns the facets of the convex hull, and the face normals. In FIG. 3, convhulln applied to points $P_1$, $P_2$, and $P_3$ returns the connectivity indicated by the dashed lines. Only the lower facets are used as the upper approximation to the PS, so in this case, facets [$P_1$, $P_3$] and [$P_3$, $P_2$] are used, and facet [$P_1$, $P_2$] is thrown away.

Facet rejection in this 2D example is straightforward and could be done by looking at the normal vector of each facet. Using the convention that normals point into the convex hull polygon, a facet the normal to which consists of all negative components could be removed. However, in higher dimensions, this simple approach is not desirable, and whether a facet of the convhulln output should be kept or removed is unclear. For example, consider the 3D PS shown in FIG. 4, where any facet consisting of anchor points and edge points, for example, along the front edge, will have a mixed normal. That is it will have some positive components and some negative.

In dimensions over 2, it is convenient to think of facets belonging to one of three categories. The first category includes facets that have strictly positive components for their normal vector. These facets are the true upper approximation facets to the PS. Specifically, all of the points belonging to such a facet are not dominated by any point in the current Pareto set, the current vertices. The second category includes facets with some positive and some negative normal vector components. In these facets, the vertices are Pareto optimal, but each interior point is dominated by one of the vertices of that facet. While such a facet might not make sense as an upper approximation, it can still be a useful generating facet. That is, a facet that may generate further PS points. The third category includes facets with all negative normal components. The facet connecting the anchor points is frequently of this type. Facets of this type are not useful for generating new points and are discarded.

Even with this categorization, many facets during the course of the algorithm will be in a gray zone regarding their usefulness for PS point generation. Rather than a fuzzy evaluation based on how many normal components are negative, how negative are they, and the like, acceptance and rejection can be based on whether or not the lower bound vertex hyperplanes can be intersected, as described next.

Referring to FIG. 1, the process continues by calculating the lower distal points at process block 14. Recalling that hyperplanes through the PS points, with normals vectors equal to the weight vector w yielding that point, are lower bounds of the PS. To find the maximal distance between the upper facets and the associated lower bounds, the position of the LDP associated with each facet that has not already been discarded due to an all negative normal vector is calculated. The facet $[P_1, P_2]$ in FIG. 3 has an all negative normal vector, and so a LDP is not calculated for it. The LDPs in FIG. 3 are the points $I_1$ and $I_2$. For each facet, the LDP is calculated by intersecting the lower bound hyperplanes at each vertex, provided these N hyperplanes intersect in a unique point. The lower bound hyperplane at a point P with normal $\vec{n}$ is given by $\vec{n} \cdot (\vec{F} - \vec{P}) = 0$. Solving N of these equations, from the N vertices of a facet, for the vector $\vec{F}$, produces the LDP for that facet. If the N hyperplanes do not intersect, or intersect nonuniquely, the facet is handled as a boundary facet, as described below.

Preferably, the location of the LDP will be checked to make sure it is within the bounding box of the PS since, at edge facets in particular, the hyperplane intersection LDP may be far from the actual PS, and should therefore be discarded. The difficulty is, while the anchor points give the lower extent of the PS, it is nontrivial to obtain the maximal extent in each dimension. Often though, as evidenced through empirical observation, the upper extent for each dimension will be simply the maximum coordinate of the points already found.

Thereafter, at process block 16, the distances from the upper approximation facets to the LDPs are calculated. This step calculates the distance from each upper bound facet, for example, $[P_1, P_3]$ to its associated LDP, for example, $I_1$. The following formula gives the distance d from a point l, which is the LDP from the previous step, to a hyperplane with normal $\vec{n}$ given by the equation $\vec{n} \cdot \vec{F} = c$:

$$d = \text{abs}[(\vec{n} \cdot \vec{l} - c)/\|\vec{n}\|] \qquad \text{Eqn. 4;}$$

Where $\|\cdot\|$ denotes the Euclidean norm of the vector and "abs" denotes the absolute value. Thus, to use Eqn. 4, the normal $\vec{n}$ of a hyperplane defined by N vertices is needed, which is available from the output of convhulln. If not available, the normal vectors are not returned, it can be calculated as follows.

For N linearly independent points in ND, the normal to their hyperplane is the null space of N−1 linearly independent vectors in the hyperplane. Choosing one vertex arbitrarily, and forming the other N−1 differences, the normal is calculated as the nullspace of these differences. The constant c in the hyperplane equation is calculated using any of the N vertices $\vec{V}$: $c = \vec{n} \cdot \vec{V}$.

This distance calculation is done for every facet that was not removed at process block 12, and that has a LDP in the bounding box of the current PS. If, at decision block 18, the maximum distance is below the stopping threshold, and the boundary option is turned off, the algorithm is finished at this point.

However, as long as there are facets with d greater than the stop tolerance, then the facet with the largest d is the next facet to run. Thus, the process then looks to the next facet to run at process block 20. Once d is below the tolerance, a check is made to determine if there are boundary facets at decision block 22. If d is below the tolerance, the algorithm terminates if the user has selected the no boundary option (or, as explained below, if no additional facets still need to be run).

Otherwise, if there are boundary facets, the one with the smallest angle is chosen to run next. The angle for a facet is defined as the angle between the facet normal vector $\vec{n}$ and the average of the vertex weight vectors $\vec{w}$. The choice to select the smallest angle facet stems from the observation that for facets flush with the PS, $\vec{n}$ and $\vec{w}$ are in roughly the same direction, as opposed to, say, the facet that connects the anchor points, in which $\vec{n}$ and $\vec{w}$ point in opposite directions, see FIGS. 2 and 3.

At process block 24, the process begins computing the next $\vec{w}$ and running it. Given the next facet to run, there are two logical choices for the next $\vec{w}$ to run. One choice is to use the normal of the facet hyperplane for $\vec{w}$. This method is problematic if the hyperplane normal has negative components. An alternate method is to use a weighted combination of the vertex weight vectors. Rather than the average of the vertex weight vectors, a weight vector is used that is a convex combination of the vertex $\vec{w}_i$'s that is maximally different from the vertex $\vec{w}_i$'s. To see why this choice is sensible over using the average, consider a 3D problem with three vertexes $\vec{w}_i$'s that are linearly dependent. Say $\vec{w}_3$ is the average of $\vec{w}_1$ and $\vec{w}_2$, then the average of all three vectors will be $\vec{w}_3$, and it would be desirable to choose a new and maximally different $\vec{w}$. In practice, a workable approach is to use the hyperplane normal if it is non-negative in all components, otherwise use the vertex maximally different $\vec{w}$, which is found by simple nonlinear optimization.

Having selected a new $\vec{w}$, and checking that it has not already been run, it is in problem 2. This gives a point on the PS that is added to the existing set of points and the algorithm returns to process block 12. It is possible that the new point has already been found, in which case the facet used to generate the new point is flagged so as not to be run again.

When the individual objective functions are of different magnitudes, the dimensions should be scaled so that, for example, distance calculations between the LDPs and hyperplanes are not dominated by the large magnitude objective function(s). This is done by mapping each objective value into [0, 1] by using its minimum and maximum value on the PS. The minimum values are the anchor points, calculated at process block 10. The maximum values, while not known, can be replaced by the current maximum values attained. Letting $L_i$ and $U_i$ denote the minimum and maximum levels of objective function, the normalization of a point P on the PS is given by:

$$\bar{P}_i = \frac{P_i - L_i}{U_i - L_i}, i = 1 \ldots N. \qquad \text{Eqn. 5}$$

After the algorithm terminates, there is a simple way to increase the density of points on the PS that takes advantage of the problem convexity. Consider a facet of the upper approximation consisting of vertices with associated beamlet intensity solutions denoted $x_i$. Let $x = 1/n \Sigma x_i$ be the weighted average beamlet intensity vector, which is a feasible solution. The convexity assumptions on the $F_j$ functions yield that for each objective function j we have $F_j(x) \leqq 1/n\Sigma F_j(x_i)$. That is, the point in objective function space that is obtained by evaluating the objective functions at an x, which is in the center of each facet is at least as good as the linear facet approximation.

The facet approximation is an upper approximation to the PS, exact at the vertex points. With the above observation, The upper approximation method can be improved by evaluating the objective functions at facet centers, or anywhere else on the facet. This can be done to as fine as resolution as desired. While the new points are not guaranteed to be on the PS, they are at least as good as our original facet-based upper approximation.

Figure 4:
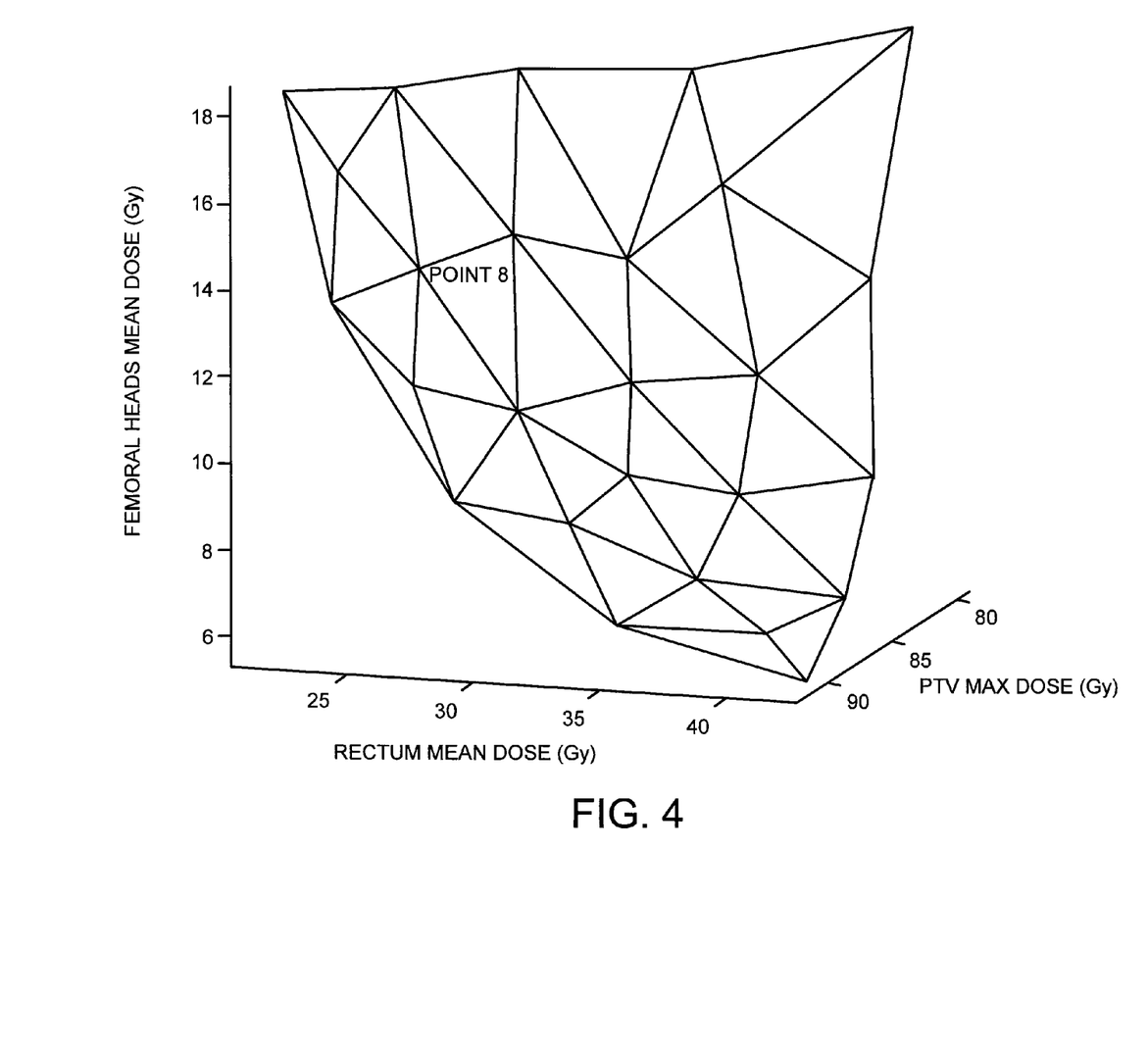
FIG. 4 is a representation of a 3D PS prepared for planning a treatment plan for a prostate.

Referring now to FIG. 4, an illustration of 3D PS for treating a prostate is shown. The vertices of the triangular facets are the computed Pareto optimal points. The vertex labeled point 8 is selected as a good compromise plan.

Hence, the above-described provides an algorithm for calculating well-placed points on a PS, and applying it to the IMRT planning problem. The algorithm can be implemented in software that is run by a computerized system. The algorithm relies on the feasible set and objective functions being convex, and in particular this is satisfied by staying within a linear programming environment. The sandwiching technique for finding upper and lower bounds for the surface allows the PS to be iteratively approximated to any specified degree of exactness. The algorithm specifies how to add a single point to the surface to best reduce the surface position uncertainty. These benefits are not available in the normal constraint method, the normal boundary intersection method, the epsilon constraint method, or the uniform weights scalarization approach.

The benefits of linear programming formulations are that they can be solved to optimality, although without special implementations this can be time intensive, and hard constraints can be imposed. Hard constraints can be used to reduce the dimensionality of the Pareto tradeoff by modeling some organs with constraints instead of objectives. However, hard constraints, for example, minimum and maximum tumor doses, can lead to infeasibility, which then requires human intervention time that the present invention seeks to reduce or eliminate. A typical single run takes between 10 and 30 min with a Pentium 4 with 2 GB of random access memory. Assuming two runs per hour, this means 30 solutions over a 15 hour period, such as overnight, which is enough to populate a 3D surface but probably a little sparse for a 4D surface. Linear optimization software that has been customized to IMRT facilitates the computation of higher dimensional PS, such as 5 or more dimensions.

The use of convex hulling to triangulate the current points on the surface also places a similar restriction of the dimensionality of the problem, since convex hulling time and the number of facets goes up exponentially with dimension. However, there is not a major drawback to restricting the number of objectives to fewer than six since currently, tradeoff surfaces are not used at all in treatment planning, and so showing tradeoffs even in 2-5 dimensions may be a useful addition. Furthermore, many clinical IMRT cases have important tradeoffs amongst only a few volumes-of-interest (VOIs). If the number of VOIs is truly greater than 5, and it is not known which ones offer the most clinically relevant tradeoffs, a hybrid LO/PS generation approach could include an initial set of runs to find nontrivial bounds for some of the VOIs, with these bounds then serving as constraints for the subsequent PS generation.

Alternatively, a PS generation approach could utilize nonlinear programming and avoid convex hulling, thus making it scale into higher tradeoff dimensions more easily. In the linear programming setting, one can trade off two objectives and put hard constraints on all the others, and therefore produce a convex tradeoff PS for visual inspection. One downside of the nonlinear approach is the difficulty of trading off a small number of objectives, say two, while constraining the other structures for clinical feasibility. Since constraints are handled by a penalty method in most large-scale nonlinear solvers, constraints are put into the objectives with high weights, while smaller weights are put on the normal objectives. As the weights are changed to populate the PS the relative weights between the objectives and the penalized constraints are changing. This causes each calculated point to be on a different slice of the expanded PS, meaning the PS which includes the constraints as penalty objectives. When such points are projected to the original, non-expanded, tradeoff space, they will not fall on a convex surface. To see this, imagine projecting points from a 3D convex Pareto surface onto two of the dimensions. The resulting points do not fall on a convex 2D curve. While still potentially practical, this makes nonlinear approaches difficult to visualize. Due to the infancy of multicriteria optimization in IMRT planning, the visualization of tradeoff surfaces is typically especially important.

The present invention adopts a scalarization approach for the MCO. In addition to the two advantages already discussed, good individual run speed and the fact that current single objective TPS systems use scalarization approaches, the scalarization approach naturally finds kinks in the PS, as seen in the geometry of the approach. If point $P_3$ was at a kink, then a large range of $\vec{w}$'s would detect it, thus making it an early point found. This is a major benefit for approximating the PS with few points.

The motivation for computing a database of Pareto optimal plans comes from the observation that planners spend a lot of time tweaking input parameters until a suitable plan is found. In forming a PS of plans, a set of input parameters is automatically run, avoiding the human iteration loop. PS's by definition, however, are formed by adjusting the relative weights between objective functions, but in practice planners adjust internal function parameters as well. For example, a planner using a one-sided quadratic penalty term for an OAR has the freedom to adjust the weight on the objective function, the power, 2 for quadratic, 3 for cubic, and the like, and the threshold dose below which a voxel's contribution is 0. New approaches that address how to automatically adjusts function parameters in addition to weights to produce a database of useful solutions may prove very useful to the field.

The present invention has been described in terms of the various aspects and features, and it should be appreciated that many equivalents, alternatives, variations, and modifications, aside from those expressly stated, are possible and within the scope of the invention. Therefore, the invention should not be limited to a particular described embodiment.

The invention claimed is:

1. A computer program product for selecting a desired portion of a subject to receive a radiation dose, the computer program product comprising a computer usable tangible non-transitory medium having a computer readable program code thereon, the computer readable program comprising program codes for:

a) selecting a plurality of points on a Pareto surface (PS) using a plurality of weight factors, wherein weight factors corresponding to an objective function of the PS that is being minimized are set to a first value while weight factors corresponding to all other objective functions of the PS are set to a second value;

b) iteratively choosing additional weight factors to run to build up a model of the PS;

c) examining each point that has been found on the PS along with the weight factor used to produce the point to determine if the point is indicated a Pareto optimal;

d) identifying new weight factors including a weight factor chosen to be such a convex combination of weight factors of vertices of the PS that is different from the weight factors of said vertices; and e) repeating steps a) through d) using the new weight factors until a Pareto optimal stop tolerance is met.

2. The computer program product of claim 1 wherein step b) includes performing a convex combination of the plurality of points to select an upper bound of the PS.

3. The computer program product of claim 1, wherein step b) includes performing a convex hulling to obtain a facet representation of the PS, said facet representation including triangular facets having vertices that are PS optimal points.

4. The computer program product of claim 3, wherein step c) includes determining lower distal points (LDPs) respectively corresponding to said facets, calculating distances separating the LDPs and the corresponding facets, and comparing these distances to a threshold value.

5. The computer program product of claim 4, wherein the Pareto optimal stop tolerance is met when each of said calculated distances is below the threshold value.

6. The computer program product of claim 1, wherein
step b) includes performing a convex combination of the plurality of points to select an upper bound of the PS, wherein the PS is sandwiched between the upper and lower bounds,
step c) includes comparing the lower bounds and upper bounds to identify a location where a gap between the lower bounds and upper bounds is largest, and
step d) includes selecting the new weights factors to add new points to the PS about the location.

7. A system for selecting a desired portion of a subject to receive a radiation dose comprising:
a computer, and
a non-transitory computer readable medium having computer readable program code disposed therein, said computer readable program code comprising a series of computer readable program steps to optimize, with the use of the computer, said radiation dose by
a) selecting a lower bound and an upper bound to sandwich a PS therebetween, the PS having a plurality of points about a desired portion of the subject selected using a plurality of weights, wherein at least some points from the plurality of points are selected by minimizing each objective function defined by the PS with weights set to a first value while weights corresponding to objective functions not being minimized are set to a second value;
b) performing a convex hulling to obtain a facet representation of the PS;
c) determining lower distal point (LDP) for each facet;
d) calculating a distance from each facet to each LDP;
e) comparing the distance to a threshold value; and
f) repeating steps a) through e) until the distance is below the threshold value for all sides of the PS.

8. The system of claim 7, wherein the series of computer readable program steps further effects step g) determining an additional point on the PS and repeating steps b) through f) using the additional point on the PS.

9. The system of claim 8 wherein step g) includes selecting a weight vector and running the weight vector to determine the additional point on the PS.

10. The system of claim 7 wherein step a) includes selecting a plurality of points and performing a convex combination of the plurality of points to select the upper bound of the PS.

11. The system of claim 10 wherein step a) includes identifying a hyperplane through each of the plurality of points and a normal vector to find the lower bound of the PS.

12. The system of claim 7, wherein step e) includes selecting the weights to add new points to the PS about the area where a gap between the lower bounds and upper bounds are largest.

13. The system of claim 7 wherein the threshold value includes a user selected threshold value.

14. The system of claim 7 wherein the PS is selected for intensity modulated radiation therapy (IMRT) planning.

15. A system for selecting a desired portion of a subject to receive a radiation dose, the system comprising:
a computer having a computer program that when executed causes the computer to:
a) select a plurality of points believed to be on a Pareto surface (PS) about the desired portion of the subject using a plurality of weights, wherein at least some points from the plurality of points are selected by minimizing each objective function defined by the PS with weights set to a first value while weights corresponding to objective functions not being minimized are set to a second value;
b) iteratively choose additional weights to run to build up a model of the PS;
c) examine each point that has been selected along with the weights used to produce the point;
d) identify new weights including a weight corresponding to a weight vector chosen to be such a convex combination of weight vectors of vertices of the PS that is different from the weight vectors of said vertices; and
e) repeat steps a) through d) using the new weights until a geometric stop tolerance is met.

16. The system of claim 15, wherein the computer is further caused to perform a convex combination of the plurality of points to (i) select an upper bound of the PS, and (ii) identify a hyperplane through each point from the plurality of points and a normal vector to such hyperplane, to find a lower bound of the PS, the PS located between the lower and upper bounds.

17. The system of claim 16, wherein the computer is further caused to compare the lower and upper bounds to identify an area where a gap between the lower and upper bounds is the largest and, if the gap exceeds a threshold value, to select new weights to add new points to the PS about the area.

18. A method for selecting a desired portion of a subject to receive a radiation dose, the method comprising:
providing a computer system; and
with the use of said computer system, receiving data associated with the radiation dose and processing the received data by
a) selecting-surface points of a Pareto surface (PS) that defines objective functions, said surface points including, for each of the objective functions,
anchor points calculated by minimizing each objective function, wherein weight factors corresponding to an objective function being minimized are set to a first value while weight factors corresponding to all other objective functions are set to a second value; and
an interior vertex point between said anchor points;
b) determining a lower bound of the PS by defining planes each of which is tangential to the PS at the corresponding surface point and has a normal vector equal to a weight factor yielding the corresponding surface point;

c) based on at least some of the surface points, determining a convex polygon having facets, said convex polygon defining an upper bound of the PS;

d) determining lower distal points of said lower bound, said lower distal points being respectively associated with corresponding facets of said convex polygon; and e) increasing a number of points of the PS by adding an interior vertex point between surface points that define a chosen facet of said convex polygon.

19. The method according to claim 18, wherein selecting surface points of a PS includes selecting an interior vertex point by one of using equal weights on each objective function and using an outward-facing normal of a plane through the anchor points.

20. The method according to claim 18, wherein determining a lower bound of the PS includes determining a lower bound wherein each of the weight factors yielding the corresponding surface point is positive.

21. The method according to claim 18 wherein determining a convex polygon includes calculating a convex hull each of facets of which defines a normal vector having at least one positive component.

22. The method according to claim 18, wherein determining lower distal points includes determining lower distal points corresponding to intersections of the planes defining the lower bound of the PS.

23. The method according to claim 18, wherein increasing a number of points of the PS includes adding an interior vertex point between such surface points that define a triangular facet the distance from which to a corresponding lower distal point is maximal and exceeds a threshold value.

24. The method according to claim 18, further comprising f) repeating steps b) through e) until each of distances between facets and corresponding lower distal points are below a threshold value.

25. The method according to claim 18, wherein increasing a number of points of the PS includes adding an interior vertex point having a weight vector that is defined by such a convex combination of vertex weight vectors that is maximally different from the vertex weight vectors.

* * * * *